US008468889B2

(12) United States Patent
Schubert et al.

(10) Patent No.: US 8,468,889 B2
(45) Date of Patent: Jun. 25, 2013

(54) APPARATUS FOR THE NON-DESTRUCTIVE TESTING OF SAMPLES USING ULTRASONIC WAVES

(75) Inventors: Frank Schubert, Dresden (DE); Abdelmalek Bouhadjera, Jijel (DZ)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 223 days.

(21) Appl. No.: 12/737,860

(22) PCT Filed: Sep. 1, 2009

(86) PCT No.: PCT/DE2009/001256
§ 371 (c)(1),
(2), (4) Date: Mar. 28, 2011

(87) PCT Pub. No.: WO2010/025717
PCT Pub. Date: Mar. 11, 2010

(65) Prior Publication Data
US 2011/0179873 A1     Jul. 28, 2011

(30) Foreign Application Priority Data
Sep. 3, 2008 (DE) .......................... 10 2008 045 485

(51) Int. Cl.
*G01N 29/07* (2006.01)
(52) U.S. Cl.
USPC .......................................................... 73/597
(58) Field of Classification Search
USPC .................. 73/597, 622, 624, 625, 628, 641, 73/644
See application file for complete search history.

(56) References Cited

U.S. PATENT DOCUMENTS

| 4,701,031 | A * | 10/1987 | Penney et al. ................. 359/305 |
| 6,588,269 | B1 * | 7/2003 | Benghezal et al. ......... 73/290 V |
| 7,410,469 | B1 * | 8/2008 | Talish et al. ...................... 601/2 |
| 7,468,263 | B2 * | 12/2008 | Kishida et al. ............. 435/173.8 |
| 8,133,191 | B2 * | 3/2012 | Rosenberg et al. .............. 601/2 |
| 2012/0086938 | A1 * | 4/2012 | Folkenberg ................... 356/246 |

FOREIGN PATENT DOCUMENTS

| DE | 101 43 755 C1 | 12/2002 |
| FR | 1 065 907 A | 5/1954 |
| GB | 2 215 056 A | 9/1989 |

OTHER PUBLICATIONS

Gregory, A.R., et al; Dual-Mode Ultrasonic Apparatus for Measuring Compressional and Shear Wave Velocities of Rock Samples; IEEE Transactions on Sonics and Ultrasonics; Apr. 1970, pp. 77-85, vol. SU-17, No. 2; XP002585368.
Bouhadjera, A., et al; High-frequency ultrasonic testing of young cement-based materials using the "prism technique"; NDT & E International; Mar. 1, 2005; pp. 135-142; vol. 38, No. 2; Butterworth-Heinemann, Oxford, GB; XP004663155.

* cited by examiner

*Primary Examiner* — J M Saint Surin
(74) *Attorney, Agent, or Firm* — Marshall & Melhorn, LLC (57) ABSTRACT

An apparatus provides for the non-destructive testing of samples. The samples can in this respect also be formed from critical materials which change their properties during manufacture, for example on a hardening or solidification. In an apparatus in accordance with the invention, at least one ultrasonic pressure wave transducer is arranged at a forward cell. The forward cell is filled with a liquid and is placed with an open side at one side onto a surface (A) of a conversion prism, in the form of a solid body, so that the liquid and the surface (A) are in touching contact. The conversion prism is placed with a further surface (B) onto a surface of a sample to be tested. At least one ultrasonic pressure wave transducer can be positioned or is positioned at the forward cell at at least two positions (T1, T2) so that the positions are arranged at an equal spacing from the center of the surface (A) of the conversion prism, said surface being placed onto the sample.

10 Claims, 5 Drawing Sheets

APPARATUS FOR THE NON-DESTRUCTIVE TESTING OF SAMPLES USING ULTRASONIC WAVES

BACKGROUND OF THE INVENTION

The invention relates to an apparatus for the non-destructive testing of samples. The samples can in this respect also be formed from critical materials which change their properties during manufacture, for example on a hardening or solidification.

The invention can furthermore be used to characterize other materials which pass through a phase transition or which change as a consequence of other mechanical, thermal, chemical or biological processes. Use is, however, also possible on solid bodies, already solidified or hardened samples.

The exact course of the solidification process or of the hardening process of materials such as cement, mortar, plaster and concrete plays a decisive role in deciding whether the fully hardened construction element has reached its planned mechanical properties, in particular its strength, or not. Since the hardening process depends on a number of parameters such as on the capacities of the concrete mixer, on the properties of the starting products (cement, aggregates, additives), on the water-to-cement ratio, on the environmental temperature, on the humidity, on the incident solar radiation, etc., the conditions for the hardening can never be kept perfectly constant, which has the consequence of fluctuating material qualities. To determine the actual course of the solidification process or of the hardening process and the quality of the respective hardened materials, inexpensive and portable test processes are therefore required which measure physical parameters, which have a sufficiently good correlation to the mechanical material properties, over the total duration of the hardening. These parameters can e.g. be the speed and the damping of ultrasonic pressure waves and shear waves or the moisture content.

A simple, widespread method in the construction industry is the removal of small core samples which are subsequently subjected to further tests such as tensile tests and bending tests in the laboratory. This method cannot be carried out in a non-destructive manner. The core samples can only be removed at a few points of the construction element. The drilled holes have to be filled again after thee removal. The core samples can moreover only be removed and examined in a largely hardened state. The important early stages of the hardening process and its total course remain out of consideration.

A rebound hammer, also called a Schmidt hammer, is suitable for the non-destructive testing of the compressive strength of concrete. It has the disadvantage that measurements are only possible at points of the surface and it can only be sensibly used in the late stage of the hardening process.

Non-destructive test processes which can also be used in early stages of the hardening process and can thus monitor the whole hardening course are usually based on ultrasound technology. In this respect, ultrasonic waves in the kHz to MHz frequency spectrum are coupled into the construction element and/or detected and evaluated via permanently applied transducers which are usually piezoelectric. In this respect, different ultrasound parameters can be correlated with the strength properties of the materials as well as in particular with characteristic stages of the hardening process. In principle, measurements are possible at small, isolated material samples (usually small cubes), but also directly on the real construction element. Various processes have been described in the technical literature. They can roughly be divided into reflection processes in which the reflected echoes reflected from the (accessible) surface of the construction element, from its rear wall or from components located in the construction element are evaluated;

transmission processes in which the waves passing through the construction element are evaluated;

Rayleigh wave processes which utilize the surface waves directed at the surface of the construction element;

resonance or impact echo processes in which natural resonances—in particular thickness resonances—of the examined construction element are measured; and sound emission processes in which the sound emissions occurring during the hardening process in the construction element volume and generated by structural conversion and shrinking are detected.

A plurality of material parameters (inter alia dependent on the frequency and the load) relevant to the material quality can be determined using these processes. In most cases, they are the sound velocity of pressure waves and shear waves (either directly via time of flight measurements or indirectly from amplitude reflection coefficients via the acoustic impedance) as well as from their damping constants. In addition, there are the corresponding Rayleigh wave parameters (sound velocity and damping) which are, however, directly linked with the elastic modulus of the pressure waves and shear waves.

None of the named processes is, however, currently able to determine the two parameters of sound velocity and damping for both types of waves and both for a reflection arrangement and a transmission arrangement (i.e. for surface testing and for volume testing). Usually only one wave mode is used (usually the pressure wave) and only surface properties or volume properties are determined. All arrangements can admittedly be combined with one another in principle, but additional (shear) transducers and measurement installations are required for this purpose. This increases the complexity and thus also the costs for the total structure, which is in particular a problem in the construction industry. If moreover two transducers are integrated in a measuring cell, two different routes have as a rule to be accepted for pressure waves and shear waves with a simultaneous measurement, which causes problems with heterogeneous media such as concrete since the material parameters scatter statistically along different routes.

The so-called prism technique is known from GB 2 215 056 A with which the measurement of sound velocities for pressure waves and shear waves can be realized with only a single (pressure wave) test head and for one and the same route. In this process, the material sample does not comprise a cube, as is the case for many standard concrete tests, but is rather a prism. By changing the angle of incidence of the pressure waves incident onto the prism base from a water bath, pressure waves and shear waves can be generated in a simple manner in the interior of the sample which are incident on the side surfaces of the prism in a perpendicular manner, are reflected there and subsequently return to the transducer on the same path. The special form of the sample allows the associated sound velocities to be determined only via the times of flight of reflected pressure waves and shear waves which are easy to measure and thus allows the Poisson number of the material to be determined via the known density of the pressure modulus and shear modulus or the elastic modulus.

The advantages of the prism method over traditional goniometer arrangements and over other processes for generating shear waves are described in detail therein.

However, only volume properties of the sample can be determined using the prism technique since only the waves passing through the material are evaluated. A second transducer would be necessary to determine surface properties by means of reflection at the prism base. The decisive disadvantage of the process is, however, that the critical angles for the optimum coupling of the two wave types during the hardening have to be constantly readjusted since they are material-dependent. Unavoidable slight deviations from the optimum angle thereby occur. These deviations admittedly do not have any direct effect on the time of flight measurement, but do noticeably influence the effectiveness of the sound coupling and thus also that of the damping measurement.

It must finally be mentioned that the functioning of the prism technique is based on the special geometry of the construction element to be examined. The process thus necessarily requires an isolated and especially manufactured prism-shaped material sample. A use on the real construction element made from concrete, e.g. by means of an attachment technique, is therefore not possible.

BRIEF SUMMARY OF THE INVENTION

It is therefore the object of the invention to be able to carry out a non-destructive testing on samples by means of ultrasonic waves in which both pressure waves and shear waves can be used and in this respect the examinations can be carried out simply and flexibly on different samples.

This object is achieved in accordance with the invention by an apparatus having the features of claim 1. Advantageous embodiments and further developments of the invention can be realized using features designated in the subordinate claims.

At least one ultrasonic pressure wave transducer is arranged at a forward cell in the invention. The forward cell is filled with a liquid and is placed with an open side at one side onto a surface (A) of a conversion prism so that the liquid and the surface (A) are in touching contact. The conversion prism represents a solid body and should be formed from a homogeneous material. The conversion prism is placed in the test with a further surface (B) onto a surface of a sample to be tested.

In an alternative in accordance with the invention, a single ultrasonic pressure wave transducer (Tx) can be moved to the forward cell at at least two different positions and can emit ultrasonic waves from these positions and can also detect reflected ultrasound waves again.

In a further alternative in accordance with the invention, a respective ultrasonic pressure wave transducer can be fixedly arranged at at least two positions. The positioning is to be selected in this respect such that the respective positions have an equal spacing from the center of the surface (A) of the conversion prism which is set onto the sample.

In the invention, a measurement cell can be used with an ultrasonic pressure wave transducer (ultrasonic pulser/receiver), a digital oscillograph as well as a computer with control and evaluation software. Pulsers/receivers and digital oscillographs can also be replaced by a corresponding computer measuring board which combines the two in it.

The particular technical features of the present invention are the liquid filled forward cell open at one side and having one or two ultrasonic pressure wave transducers as well as having an optional damping element, the conversion prism likewise optionally provided with an absorber for generating pressure waves and shear waves incident onto the sample in a perpendicular manner with an identical time of flight as well as the specific sample connection with the possibility to examine special prismatic and rectangular material samples open at one side in a housing as well as real construction elements. In the ideal case, the following parameters can be determined with one and the same apparatus using the invention:

1—Sound velocity of the pressure wave in the sample volume (transmission);
2—amplitude reflection coefficient of the pressure wave;
3—sound velocity of the pressure wave at the sample surface (in this respect, the then current parameter—the velocity of the pressure wave at the sample surface—is derived from the second entry—amplitude reflection coefficient, which also applies to the following parameters);
4—sound velocity of the shear wave in the sample volume (transmission);
5—amplitude reflection coefficient of the shear wave;
6—sound velocity of the shear wave at the sample surface (derived from 5);
7—sound velocity of the surface wave (derived from 3 and 6);
8—elastic modulus and Poisson number in the sample volume (transmission, derived from 1 and 4);
9—elastic modulus and Poisson number at the sample surface (reflection, derived from 3 and 6);
10—pressure modulus and shear modules in the sample volume (transmission, derived from 1 and 4);
11—pressure modulus and shear modulus at the sample surface (reflection, derived from 3 and 6);
12—damping of the pressure wave in the sample volume (transmission); and
13—damping of the shear wave in the sample volume (transmission);

No previously known technical solution offers these possibilities in combination.

The liquid-filled forward cell open at one side and having one or two pressure wave transducers as well as an optional absorber/damping element effects a reproducible excitation and detection of ultrasonic pressure waves. The advantage is that both pressure waves and shear waves can be generated in a very simple manner in interplay with the conversion prism by mode conversion at the acoustically ideally coupled interface of liquid/prism. Interference multiple echoes in the forward cell can be effectively suppressed by optional absorbers.

The conversion prism likewise optionally provided with an absorber effects the refraction or the mode conversion of the pressure wave excited in the forward cell into a shear wave. The main advantage of this arrangement is that both excited waves (pressure wave and shear wave) corresponding to the positions T1 and T2 of the ultrasonic pressure wave transducers enter into the prism at an angle of 45° on identical paths, are subsequently incident onto the material sample in a perpendicular manner, interact therewith and subsequently pass back to the ultrasonic pressure wave transducer again on exactly the same path. This route is independent of the material parameters of the sample and thus allows a permanent, reproducible measurement during the total solidification process or hardening process.

The side surface D of the conversion prism in many cases allows the measurement of multiple echo sequences and therefore results in a higher accuracy in the measurement of the material parameters. In certain other cases in which the multiple echoes rather have an interfering effect, the side D can optionally be configured as an absorber. D1 effectively suppresses the multiple echoes and results in a better signal-to-noise ratio of the primary echo.

The special connection of the material samples via the lower side of the conversion prism also allows measurements at real construction elements both at material sheathings open at one side and having an ideal acoustic coupling to the conversion prism and by means of the attachment technique. An especially designed prismatic housing for a sample amplifies the echo signal from the sample since divergent wave portions which are not incident on the sample in an exactly perpendicular manner can also be detected. Since the sample connection is variable, rectangular housings of a simpler design can, however, also be used instead. The standardized cube samples widespread in the construction industry can thus also be examined.

In summary, it can be stated that both pressure wave properties and shear wave properties, in a transmission arrangement and in a reflection arrangement in each case, can be measured using the present invention both in the lab and in use on a building site on the basis of one and the same apparatus (measurement cell) and during the total hardening process. These measurements can be carried out fully automatically by means of computer-based control, data recording and data evaluation since only pulse-based time of flight measurements have to be carried out. An inexpensive and reliable use in the construction industry and in other applications is moreover possible due to the robust apparatus of simple structure.

The invention will be explained in more detail in the following with reference to examples.

BRIEF DESCRIPTION OF THE DRAWINGS

There are shown.

DETAILED DESCRIPTION OF THE INVENTION

Figure 1:
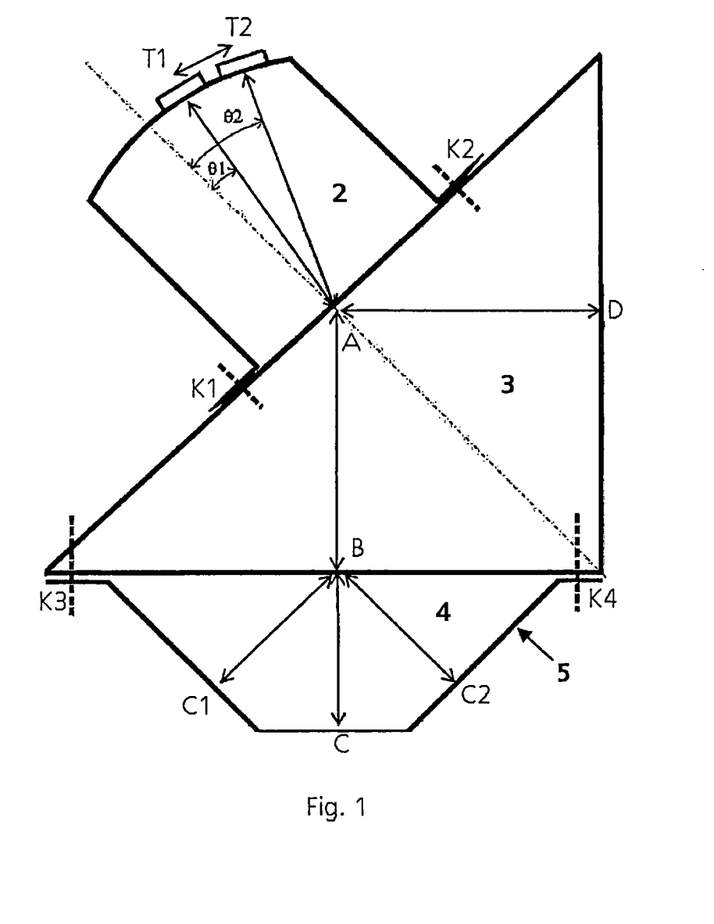
FIG. 1 a first example of an apparatus in accordance with the invention with a positionable ultrasonic pressure wave transducer.

In the example shown in FIG. 1, an ultrasonic normal wave transducer test head is present at the apparatus as an ultrasonic wave pressure transducer Tx which can acoustically generate and detect broadband pulsed signals. It is attached to the housing of a forward cell 2 open at one side and filled with liquid, wherein the active transducer surface is located within the liquid. The forward cell is connected to a fixed conversion prism 3 and is placed onto a surface. In this respect, the liquid and the surface of the conversion prism are directly in contact.

The sample 4 is received in a housing 5 open at one side in which it can also solidify and/or harden when it is a case of such a sample material.

The ultrasonic pressure wave transducer Tx can be a piezoelectric test head, e.g. an artificially or naturally focused immersion test head. In this respect, the active aperture used in the invention, the ultrasonic wave pressure transducer Tx, should be arranged in the liquid of the forward cell 2. This liquid, in which only pressure waves can propagate, is as a rule water, but other liquids can also be used in principle. Different metals can be considered as the material for the housing of the forward cell 2 such as construction steel, but also other solid bodies such as also glass-fiber-reinforced plastic (GRP) or carbon-fiber reinforced plastic (CRP).

The ultrasonic pressure wave transducer Tx can be displaced along a circular line so that the geometrical spacing from its center, from which ultrasonic waves can be emitted and can also be detected there, to the center of the base edge of the conversion prism A is always of equal size. The ultrasonic pressure wave transducer Tx can be locked in at least two positions T1 and T2. The associated angular positions $\theta 1$ and $\theta 2$ respectively correspond to the critical angles at which the coupling of the pressure wave or shear wave into the conversion prism 3 is at a maximum at an angle of reflection of 45°. The two angles of incidence $\theta 1$ and $\theta 2$ in known liquids only depend on the material properties of the conversion prism 3. A typical material for a conversion prism 3 is construction steel, but other solid materials are also possible depending on the application.

With an apparatus in accordance with the invention, the active surfaces of a respective ultrasonic pressure wave transducer Tx should be arranged at the positions T1, T2 so that the spacing from the center of the surface A is of equal size in each case.

The forward cell 2, including the ultrasonic pressure wave transducer Tx, is fixedly connected to the conversion prim 3 in fluid-tight manner by a sealed quick-clamp connection or screw connection K1 and K2 so that a direct, acoustically optimum coupling is given between the liquid and the prism material. This connection can, however, be released so that, if required, different forward cells 2 can be combined with different conversion prisms 3, with different dimensioning and with different materials.

A pressure wave (position T1) and a shear wave (position T2) respectively is generated at the interface between the forward liquid and the conversion prism 3 at A in dependence on the position of the ultrasonic pressure wave transducer Tx, said pressure wave or shear wave being refracted at an angle of 45° to the axis of incidence into the conversion prism 3. It must be emphasized in this respect that an exact observation of the critical angle of incidence is not absolutely necessary in the present case, in contrast to goniometer arrangements. Due to the more or less pronounced focusing of the ultrasonic wave beam, there are already always wave portions in the "vicinity" of the critical angle of incidence which are refracted at the "correct" angle of 45° into the conversion prism 3.

After passing through the water/prism interface A, the respective wave (pressure wave or shear wave) is incident onto the surface B of the conversion prism 3 in a perpendicular manner, said surface being in direct contact with the optionally solidifying and/or hardening material of the sample 4. Both a reflection and a transmission of the respective wave type takes place at this interface. It is now necessary to distinguish two routes of the ultrasonic waves:

Route 1:

The portion transmitted at B continues on through the material and is totally reflected at the rear interface C of the housing 5. The wave thereafter returns again, passes (partially) through the surface B of the conversion prism 3 again, is (partially) refracted back into the liquid contained in the forward cell 2 at the surface A as a pressure wave and can finally be detected at the position T1 or T2 of the ultrasonic pressure wave transducer Tx as an echo signal.

The effective sound velocity of the material of the sample 4, averaged over the path BC covered in the sample 4, can be calculated from the time of flight of the echo of the reflected ultrasonic waves having the route Tx-A-B-C-B-A-Tx, the known paths in the forward cell 2 (TxA), in the conversion prism 3 (AB) and in the sample (BC) and the known sound velocities in the liquid and in the prism material.

The effective sound absorption of the material can in turn be calculated from the amplitude of the detected echo via the comparison with a (known) reference sample. Both determined parameters thus reflect volume properties of the material.

The housing 5 for the sample 4 is fixedly connected to the conversion prism (K3 and K4), wherein the solidifying or hardening material is in direct contact with the surface B of the conversion prism 3. This connection can likewise be released so that different prisms can be connected to different housings 5.

Figure 2:
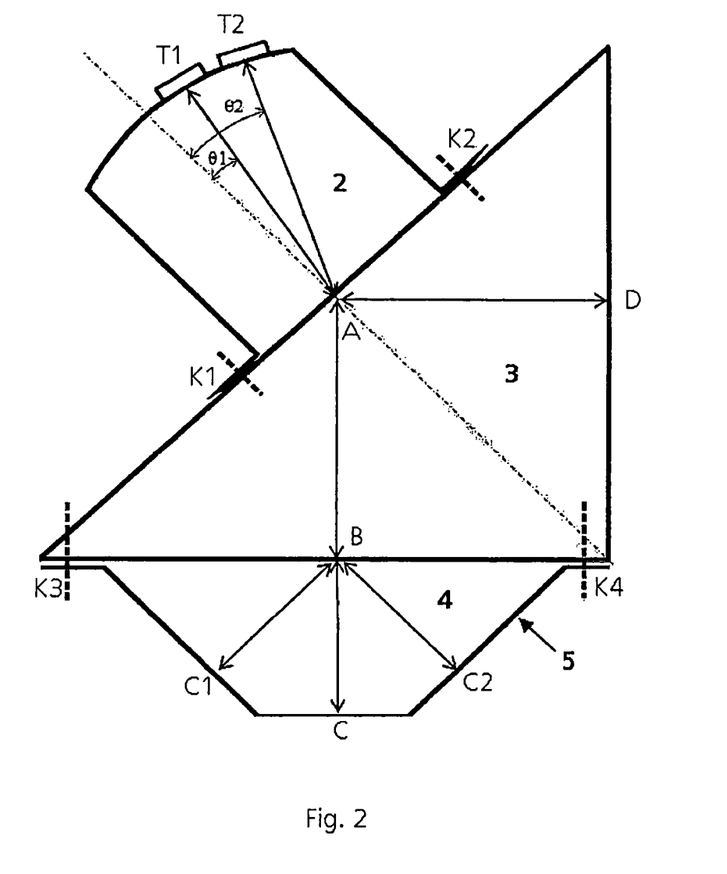
FIG. 2 a second example of an apparatus in accordance with the invention with two ultrasonic pressure wave transducers fixedly installed at two positions.

The housing 5 is prismatically configured in the examples shown in FIGS. 1 and 2. However, the tip of the sheathing is cut off such that the paths BC1 and BC2 in each case have the same length as the path BC and a trapezoidal shape is obtained. Divergent wave portions are thus also detected which are not refracted exactly at a 45° angle at the surface A and consequently do not pass through the interface in an exactly perpendicular manner at the surface B. These divergent portions, however, are incident to the surfaces C1 and C2 of the housing 5 in a partly perpendicular manner and are there totally reflected. The signal-to-noise ratio can be further improved using these echo contributions.

Since the portions reflected back from the surfaces C, C1 and C2 of the housing 5 are not only transmitted at the surface B, but also partly reflected, multiple reflections occur between the surfaces B and C on a moderate material damping and can also be detected at the location of the ultrasonic pressure wave transducer Tx (e.g. Tx-A-B-C-B-C-B-A-Tx). These multiple echoes enable additional measurements which further increase the accuracy of the determined material parameters.

Route 2:

The portion of the ultrasonic waves reflected at the surface B is reflected back to the surface A and is refracted back there as a pressure wave (partly) into the liquid contained in the forward cell 2 and is finally detected at the location of the ultrasonic pressure wave transducer Tx. The amplitude reflection coefficient can be determined from the amplitude of the ultrasonic waves reflected at the surface B via the comparison with a total reflection at air, from the known material parameters of the liquid and from the material from which the conversion prism is formed as well as from the density of the material (which in turn results from the determined mass of the known sample volume in the housing 5), and the acoustic impedance and finally the sound velocity in the region of the sample 4 close to the surface can be determined from said amplitude reflection coefficient.

Since the wave portions returning in the conversion prism 3 are not only transmitted at the interface A, but are rather also partly reflected in the direction of the interface D, multiple reflections (e.g. Tx-A-B-A-D-A-B-A-Tx) occur which, in a similar manner to the above transmission case, result in further measured values and thus in even more accurate material parameters which can be determined.

Pressure waves are generated in the conversion prism 3 at the position T1 which take both named routes. A portion of the waves is reflected at B and the other portion is transmitted. Shear waves are emitted, reflected and transmitted in the same form from position T2.

In the example shown in FIG. 2, two similar ultrasonic pressure wave transducers Tx are already fixedly installed in the forward cell 2. In this respect, one is fixedly installed at position T1 and the other at position T2. There is thus no necessity of displacing the one ultrasonic pressure wave transducer Tx such as is necessary in the example in accordance with FIG. 1. A more robust, faster and more reproducible measurement very close to real time can be achieved with an embodiment in accordance with the example shown in FIG. 2. The forward cell 2 filled with the liquid can thus also have a simpler and less expensive configuration.

Otherwise, the statements made on the embodiment and the operability for the example in accordance with FIG. 1 also apply to this example. It is only the case that a change in the position of the ultrasonic pressure wave transducer Tx is no longer necessary. The two ultrasonic pressure wave transducers Tx at the positions T1 and T2 can be operated and used for the testing of the sample 4 in an alternating manner.

The housing 5 for the sample 4 in the examples in accordance with FIGS. 1 and 2 is configured as prismatic and in trapezoidal form in order also to detect divergent portions of the waves transmitted through the surface B. The dominant contribution of the reflection from the rear side of the housing 5 is, however, made by the ultrasonic waves reflected by the surface Cr. The prismatic geometry of the housing 5 can therefore optionally also be replaced by a simpler geometry, e.g. rectangular of already standardized cube form. In this respect, it is only important that a surface C aligned parallel to the surface B is present at the housing 5 and its distance from the surface B is known.

Figure 3:
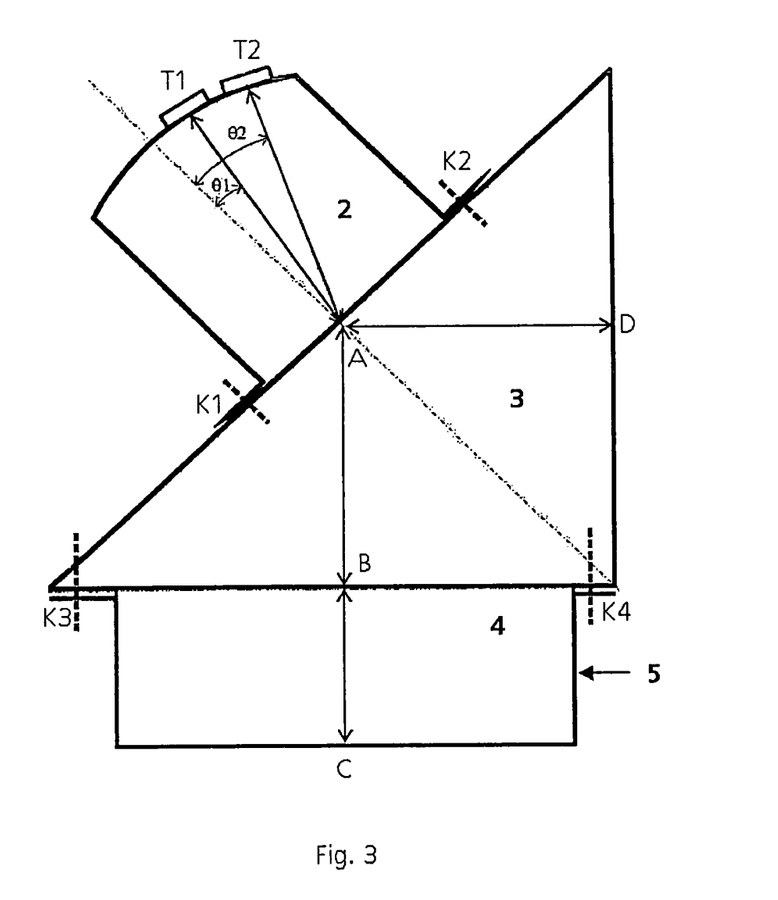
FIG. 3 a further example with two ultrasonic pressure wave transducers fixedly installed at two positions and a rectangular housing.

Except for the housing 5 configured as a rectangle and shown in FIG. 3, the apparatus can, however, be configured in accordance with the examples of FIG. 1 or 2.

Figure 4:
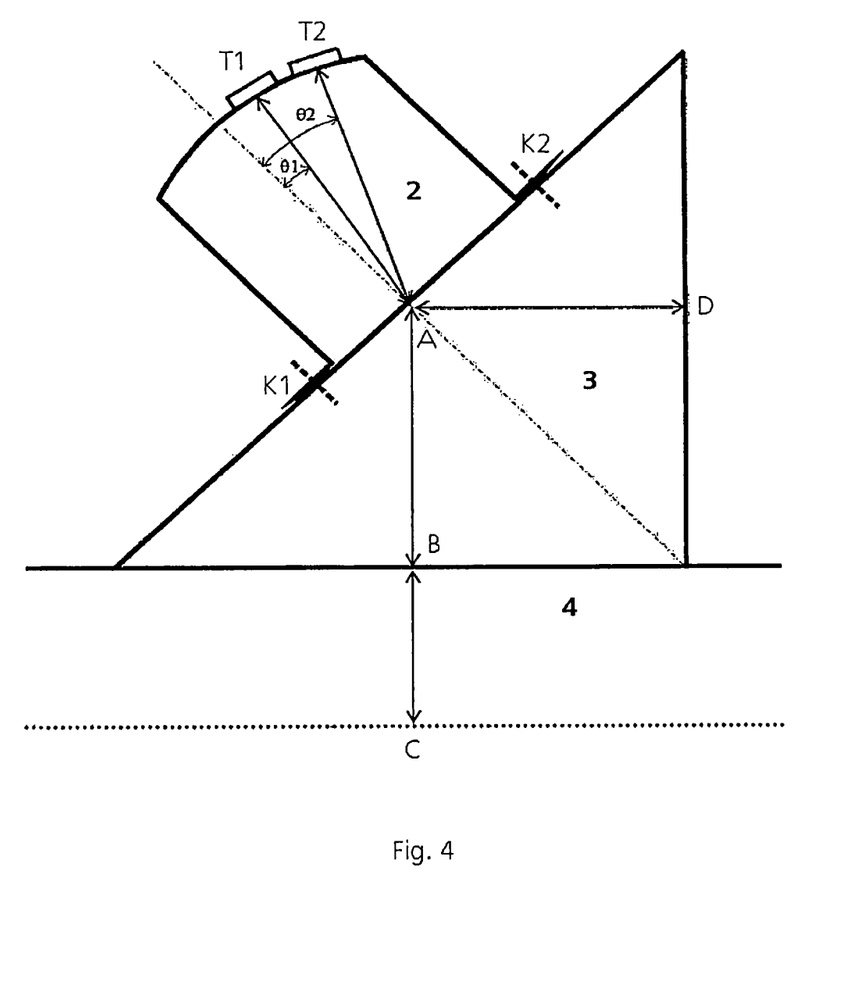
FIG. 4 a further example with two ultrasonic pressure wave transducers fixedly installed at two positions in which the apparatus is placed directly onto a material surface.

Only the sound velocity of the pressure wave or shear wave can be determined from the amplitude reflection coefficient via the route 2 described in embodiment 1, but not its damping. Instead, however, this route only requires the surface of a sample 4. The measurement can thus not only be carried out at a laboratory sample, but also at a real construction element in use at a construction site. For this purpose, only the placing of the conversion prism 3 directly onto the material surface is required, with it being necessary to observe a sufficiently good and stable acoustic coupling. If a reflection from a second interface C at a known spacing is present, transmission properties of the material can also be determined here, analog to the procedure described in the example in accordance with FIG. 1. The example in accordance with FIG. 4 can be combined as desired with the embodiments in accordance with FIG. 1 or 2.

With a large spacing of the surfaces B and C and/or with low sound velocities in the material of the sample 4, for example on the solidifying or hardening, the reflected sound waves in accordance with route 1 (Tx-A-B-C-B-A-Tx) enter the ultrasonic pressure wave transducer Tx relatively late. Superimpositions with multiple echo sequences can thereby occur which are generated by the side of the conversion prism 3 at D1 (e.g. Tx-A-B-A-D1-A-B-A-Tx) or by the upper housing side of the forward cell 2 at D2 (e.g. Tx-A-D2-A-Tx). To suppress or eliminate these interfering reflected waves, the surfaces D1 and D2 are configured as sound-absorbing in the example shown in FIG. 5. Incident ultrasonic waves are diffusely scattered in all directions and are no longer reflected as a coherent beam due to a structuring of the surface facing into the interior of the conversion prism 3, e.g. as a zig-zag pattern of the surfaces. The diffusely scattered portions are moreover attenuated by a highly absorbing material which is located behind the structured, serrated surface (e.g. modeling clay). The effect of the absorber material is based in this respect on two mechanisms. On the one hand, the effective acoustic impedance difference at the interface is considerably reduced with respect to the case of a reflection at air so that fewer wave portions are scattered back or reflected. The wave portions now penetrating more strongly into the absorber material are largely dissipated there so that significant reflections at the (smooth) rear wall of the absorber 6 can no longer occur. The absorber(s) 6 can in this respect be formed alone or also in combination with a structured surface and/or with an absorber material.

Figure 5:
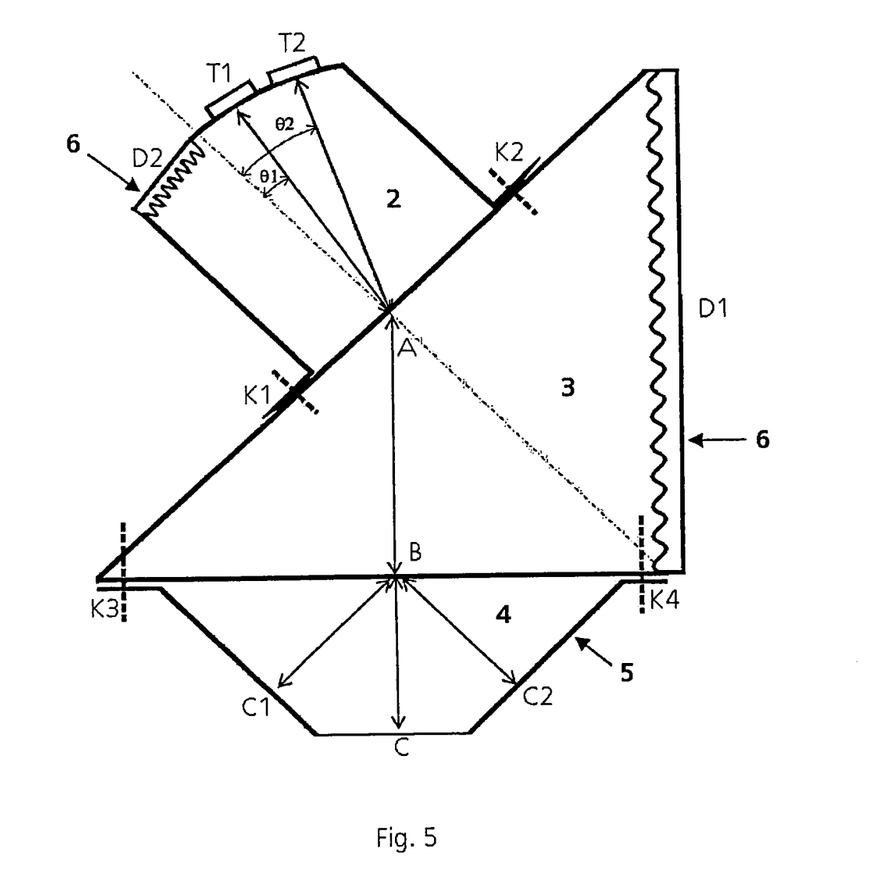
FIG. 5 a further example with ultrasound-absorbing and scattering walls.

The structured surface D1 can be formed by direct mechanical machining of the prism surface. The absorber material is applied in a flush manner thereto and optionally encased. A material more permeable to sound, i.e. provided with a low acoustic impedance (e.g. acrylic glass), can be used for the serrated surface D2 and the associated housing in the upper left corner of the forward cell 2.

Both sound-absorbing and optionally scattering surfaces D1 and D2 can be used together or also independently of one another depending on the application.

In contrast to the representation, it is not absolutely necessary to structure the total surfaces or to provide them with an absorber material at D1 and D2. It can be sufficient to restrict this to surface regions from which sound waves which may be reflected particularly interfere with the detection.

This embodiment can be combined as desired with other examples shown in FIGS. 1 to 4.

The invention claimed is:

1. An apparatus for the non-destructive testing of samples using ultrasonic waves, comprising:
   a conversion prism in the form of a solid body, the conversion prism having a surface (A) and a further surface (B);
   a forward cell, the forward cell being filled with a liquid and having an open side, wherein the open side of the forward cell is placed onto the surface (A) of the conversion prism, so that the liquid and the surface (A) are in touching contact, and wherein the conversion prism is placed with the further surface (B) onto a surface of a sample to be tested; and
   at least one ultrasonic pressure wave transducer, the ultrasonic pressure wave transducer being arranged at the forward cell; wherein
   the at least one ultrasonic pressure wave transducer at the forward cell is configured to be positioned or are positioned at at least two positions (T1, T2) at an equal spacing from the center of the surface (A) of the conversion prism, wherein the surface (B) is placed onto the sample.

2. The apparatus in accordance with claim 1, wherein the sample is received in a housing which is configured to be connected to the conversion prism and which is configured as rectangular, cuboid or prismatic.

3. The apparatus in accordance with claim 2, wherein a third surface (D) of the conversion prism and/or a surface (D2) of the housing of the forward cell, which is disposed opposite the surface (A) of the conversion prism, is/are configured as absorbing and/or scattering ultrasonic waves with an absorber.

4. The apparatus in accordance with claim 3, wherein an absorber material is applied to the third surface (D) of the conversion prism and/or the surface (D2) of the housing of the forward cell which is disposed opposite the surface (A) of the conversion prism.

5. The apparatus in accordance with claim 3, wherein the third surface (D) of the conversion prism and/or the surface (D2) of the housing of the forward cell which is disposed opposite the surface (A) of the conversion prism is/are configured in a structured manner.

6. The apparatus in accordance with claim 2, wherein the housing is designed and dimensioned so that it has surfaces (C, C1, C2) for reflecting ultrasonic waves, and each of these surfaces is equally spaced from the center of the surface (B) of the conversion prism.

7. The apparatus in accordance with claim 1, wherein the at least one ultrasonic pressure wave transducer has apertures which are arranged in the liquid contained in the forward cell.

8. The apparatus in accordance with claim 1, wherein each of the at least one ultrasonic pressure wave transducers are of the same type.

9. The apparatus in accordance with claim 1, wherein the active surface of the at least one ultrasonic pressure wave transducer is arranged at the positions (T1, T2) so that each is equidistant from the center of the surface (A).

10. The apparatus in accordance with claim 1, wherein the positions (T1, T2) are selected so that pressure waves are configured to each be emitted at an angle of 45° into the conversion prism.

* * * * *

UNITED STATES PATENT AND TRADEMARK OFFICE
CERTIFICATE OF CORRECTION

PATENT NO. : 8,468,889 B2  Page 1 of 1
APPLICATION NO. : 12/737860
DATED : June 25, 2013
INVENTOR(S) : Schubert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 249 days.

Signed and Sealed this
Eighth Day of September, 2015

Michelle K. Lee
*Director of the United States Patent and Trademark Office*